United States Patent
Kinsho et al.

(10) Patent No.: US 10,494,322 B2
(45) Date of Patent: Dec. 3, 2019

(54) METHOD FOR PRODUCING 3,7-DIMETHYL-7-OCTENOL AND METHOD FOR PRODUCING 3,7-DIMETHYL-7-OCTENYL CARBOXYLATE COMPOUND

(71) Applicant: SHIN-ETSU CHEMICAL CO., LTD., Tokyo (JP)

(72) Inventors: Takeshi Kinsho, Joetsu (JP); Tatsuya Fujii, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/219,350

(22) Filed: Dec. 13, 2018

(65) Prior Publication Data

US 2019/0194099 A1    Jun. 27, 2019

(30) Foreign Application Priority Data

Dec. 26, 2017    (JP) ................ 2017-249539

(51) Int. Cl.
    *C07C 29/40*    (2006.01)
    *C07C 67/03*    (2006.01)
    *C07C 17/263*    (2006.01)
    *C07C 67/08*    (2006.01)
    *C07C 67/14*    (2006.01)
    *C07C 67/39*    (2006.01)
    *C07C 29/09*    (2006.01)
    *C07C 21/04*    (2006.01)
    *C07C 69/007*    (2006.01)
    *C07C 33/025*    (2006.01)

(52) U.S. Cl.
CPC .......... *C07C 29/40* (2013.01); *C07C 17/2632* (2013.01); *C07C 29/095* (2013.01); *C07C 67/03* (2013.01); *C07C 67/08* (2013.01); *C07C 67/14* (2013.01); *C07C 67/39* (2013.01); *C07C 21/04* (2013.01); *C07C 33/025* (2013.01); *C07C 69/007* (2013.01)

(58) Field of Classification Search
None
See application file for complete search history.

(56) References Cited

U.S. PATENT DOCUMENTS 2,679,476 A * 5/1954 Joffre ............... C07C 29/56
                                                                                                           204/157.9
2002/0004620 A1    1/2002   Yamada et al.

FOREIGN PATENT DOCUMENTS

GB          1278178    *   6/1972
JP        2001-288130 A      10/2001

OTHER PUBLICATIONS

Eschinazi ("Structural Studies in the Citronellyl and Rhodinyl Series. The Synthesis of Rhodinal and Rhodinol" Journal of Organic Chemistry, 26, 1961, p. 3072-3076) (Year: 1961).*

Gieselmann, M. J. et al., "Sex Pheromone of the San Jose Scale", J. Chem. Ecol., vol. 5, No. 6, pp. 891-900, (1979).

Anderson, Richard J. et al., "Synthesis of 7-Methyl-3-Methylene-7-Octeni-YL Propanoate and (Z)-3,7-Dimethyl-2, 7-Octadien-I-YL Propanoate, Components of the Sex Pheromone of the San Jose Scale", J. Chem. Ecol., vol. 5, No. 6, pp. 919-927, (1979).

Anderson, R. J. et al., "Synthesis and Identification of a Third Component of the San Jose Scale Sex Pheromone", J. Chem. Ecol., vol. 7, No. 4, pp. 695-706, (1981).

(Continued)

*Primary Examiner* — Amy C Bonaparte
(74) *Attorney, Agent, or Firm* — Oliff PLC

(57) ABSTRACT

Methods selectively and efficiently produce 3,7-dimethyl-7-octenol and a carboxylic acid ester thereof. More specifically, a method produces 3,7-dimethyl-7-octenol, including steps of: subjecting a 3-methyl-3-butenyl nucleophilic reagent (2) and a 1,3-dihalo-2-methylpropane compound (3) to a coupling reaction to obtain a 2,6-dimethyl-6-heptenyl halide compound (4); converting the compound (4) into a 2,6-dimethyl-6-heptenyl nucleophilic reagent (5); and subjecting the nucleophilic reagent (5) to an addition reaction with at least one electrophilic reagent selected from the group made of formaldehyde, paraformaldehyde and 1,3,5-trioxane, followed by a hydrolysis reaction to obtain 3,7-dimethyl-7-octenol (6); and the other method.

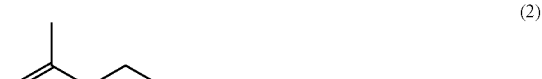

(2)

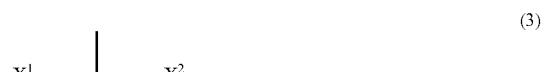

(3)

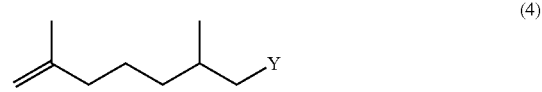

(4)

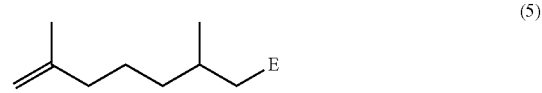

(5)

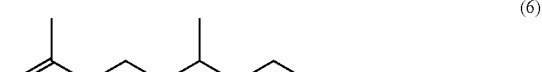

(6)

4 Claims, No Drawings

(56) References Cited

OTHER PUBLICATIONS

Ishmuratov G. Yu. et al., "Universal Approach to the Synthesis of Juvenoid Hydroprene and Methoprene from 4-Methyltetrahydropyran", Chemistry of Natural Compounds, vol. 37, No. 5, pp. 486-489, (2001).
Veselovskii, V. V. et al., "Synthesis of Linear α-Monoterpenyl Acetates From Dimethylsulfonium Precursors", Bull. Acad. Sci. USSRDiv. Chem. Sci., vol. 39, pp. 1722-1724, (1991).

\* cited by examiner

US 10,494,322 B2

METHOD FOR PRODUCING 3,7-DIMETHYL-7-OCTENOL AND METHOD FOR PRODUCING 3,7-DIMETHYL-7-OCTENYL CARBOXYLATE COMPOUND

BACKGROUND OF THE INVENTION

1. Field of the Invention

The invention relates to a method for producing 3,7-dimethyl-7-octenol and a method for producing a 3,7-dimethyl-7-octenyl carboxylate compound.

2. Related Art 3,7-Dimethyl-7-octenol has a rose-like aroma and is widely applied in floral compounded perfumes and fruit flavors.

3,7-Dimethyl-7-octenol is commercially available, but a commercial product may be an optically active scalemic mixture which has been separated from natural geranium oil and contains an excess amount of one enantiomer, or may be a mixture containing geraniol (i.e. 3,7-dimethyl-2,6-octadienol), 3,7-dimethyl-6-octanol, or linalool as an impurity. Some commercially available products of 3,7-dimethyl-7-octenol are confused in terms of product names depending on suppliers or raw materials. Products available under the name of rhodinol, α-citronellol or the like may be a mixture of (S)-3,7-dimethyl-7-octenol or 3,7-dimethyl-6-octenol as a main component with various monoterpene alcohols. Hence, chemically pure 3,7-dimethyl-7-octenol, especially the (+)-3,7-dimethyl-7-octenol, is difficult to obtain, and there is a strong demand for the method for selectively and efficiently synthesizing chemically pure (1)-3,7-dimethyl-7-octenol.

3,7-Dimethyl-7-octenyl carboxylates, which are carboxylic acid esters of 3,7-dimethyl-7-octenol, are also used as perfumes and flavors.

A sex pheromone of *Quadraspidiotus perniciosus* (generic name: San Jose Scale, hereinafter also called "SJS"), which is widely distributed in the world, damages fruit trees and ornamental trees, especially deciduous fruit trees, and is an economically critical insect pest, has been identified to contain three isomeric compounds: 7-methyl-3-methylene-7-octenyl propionate, (Z)-3,7-dimethyl-2,7-octadienyl propionate and (E)-3,7-dimethyl-2,7-octadienyl propionate, as active components by Gieselmann et al. and Anderson et al. (Gieseimam et al., J. Chem. Ecol., 5, 891 (1979), Anderson et al., J. Chem. Ecol., 5, 919 (1979), and Anderson et al., J. Chem. Ecol., 7, 695 (1981)).

A 3,7-dimethyl-7-octenyl carboxylate compound may be produced through esterification of 3,7-dimethyl-7-octenol, and from this viewpoint, an economic synthetic method of 3,7-dimethyl-7-octenol has great significance.

Synthesis examples of 3,7-dimethyl-7-octenol or 3,7-dimethyl-7-octenyl carboxylate compounds include syntheses of 3,7-dimethyl-7-octenol and 3,7-dimethyl-7-octenyl acetate by Ishmuratov et al., in which a carbonyl group of 8-acetoxy-6-methyloctan-2-one produced from 4-methyltetrahydropyran through several steps is converted into a methylene group by Wittig reaction to obtain 3,7-dimethyl-7-octenyl acetate, and the obtained acetate is hydrolyzed (Ishmuratov et al., Chemistry of Natural Compounds, 37,486 (2001)). The synthesis examples thereof also include a synthesis of 3,7-dimethyl-7-octenyl acetate by Veselovskii et al., in which dimethylsulfonium perchlorate obtained from 3,7-dimethyl-6-octenyl acetate is subjected to electron reduction to obtain 3,7-dimethyl-7-octenyl acetate (Veselovskii et al., Bull. Acad. Sci. USSRDiv. Chem. Sci., 39, 1722 (1991)). Synthesis examples of an optically active compound include a method in which a cis-3,7-dimethyl-2,6-octadienylamine is subjected to asymmetric isomerization and then subjected to hydrolysis to obtain an aldehyde, and the aldehyde is reduced to obtain a mixture containing 100 parts by weight of 3,7-dimethyl-6-octenol as a main component, and 2 to 10 parts by weight of 3,7-dimethyl-7-octenol (JP 2001-288130A).

SUMMARY OF THE INVENTION

The method for producing 3,7-dimethyl-7-octenol by Ishmuratov et al., however, requires four steps for the production, and uses silica gel column chromatography for the purification. Thus, the method involves great difficulties in synthesizing a large amount of the target compound. The method for producing 3,7-dimethyl-7-octenyl acetate by Veselovskii et al. requires, for example, electrochemical reduction using a perchlorate salt so that it is unfavorable for industrial production. The method for producing 3,7-dimethyl-7-octenol according to JP 2001-288130A produces, not as a main product, α-nerylamine, which is a precursor of 3,7-dimethyl-7-octenol; and requires four steps for the production and the recovery of an unreacted isoprene. For selective telomerization, reaction temperatures, reaction times and the like have to be strictly controlled.

As mentioned above, conventional production methods have many problems, and there is a demand for a simple method for selectively and efficiently producing 3,7-dimethyl-7-octenol.

3,7-Dimethyl-7-octenyl propionate, one of the target compounds in the invention, has a similar structure to those of the above three compounds as the sex pheromone of SJS. Thus, it is thought to exhibit pheromone activity, and expected to be used as a pheromone active substance.

In view of the above circumstances, an object of the invention is to provide simple methods for selectively and efficiently producing 3,7-dimethyl-7-octenol and a carboxylic acid ester thereof, i.e. a 3,7-dimethyl-7-octenyl carboxylate compound, both being important as perfumes.

The inventors have considered that a method of forming an exo-double bond at 7-position of 3,7-dimethyl-7-octenol, which is one of the target compounds, by a reaction with positional isomerization of a double bond (for example, isomerization reaction from a tri-substituted double bond to an exo-double bond), should be avoided because the separation between a reactant and a product of the isomerization reaction is difficult if isomerization is incomplete. If a compound having an exo-double bond which will become the exo-double bond at 7-position of a target compound is selected as the starting material, and if a reaction which may cause double-bond isomerization, for example, catalytic hydrogenation or catalytic isomerization (double-bond isomerization using a catalyst for catalytic hydrogenation) is avoided, it is considered that 3,7-dimethyl-7-octenol can be selectively produced without isomeric impurities that are difficult to separate. In order to constitute the carbon framework having 10 carbon atoms (C10 unit) of 3,7-dimethyl-7-octenol through a short process, it is considered that a straightforward binding route without many carbon chain extensions of short units, for example, a route of binding two units (for example, C5 unit and C5 unit) or a route of binding three units (for example, C5 unit, C4 unit and C1 unit), is preferred. In addition, it is advantageous that the straightforward binding route should not involve the removal of an excess carbon unit which has been bound in the route.

As a result of intensive studies in consideration of the above circumstances, the inventors have found that the 3,7-dimethyl-7-octenol can be produced at a high yield by a method in which a 3-methyl-3-butenyl nucleophilic reagent and a 1,3-dihalo-2-methylpropane compound are subjected to a coupling reaction to obtain a 2,6-dimethyl-6-heptenyl halide compound; the 2,6-dimethyl-6-heptenyl halide compound is used to prepare a 2,6-dimethyl-6-heptenyl nucleophilic reagent; and the 2,6-dimethyl-6-heptenyl nucleophilic reagent and at least one electrophilic reagent selected from the group consisting of formaldehyde, paraformaldehyde and 1,3,5-trioxane are subjected to an addition reaction and a hydrolysis reaction. The inventors also have found that esterification of 3,7-dimethyl-7-octenol yields a 3,7-dimethyl-7-octenyl carboxylate compound, and the invention has been accomplished.

In an aspect of the invention, there is provided a method for producing 3,7-dimethyl-7-octenol of Formula (6):

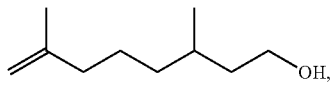

(6)

comprising steps of:
subjecting a 3-methyl-3-butenyl nucleophilic reagent of General Formula (2):

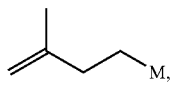

(2)

wherein M denotes Li, $MgZ^1$, $ZnZ^1$, Cu, $CuZ^1$, or $CuLiZ^1$,
wherein $Z^1$ denotes a halogen atom or a 3-methyl-3-butenyl group, and
a 1,3-dihalo-2-methylpropane compound of General Formula (3):

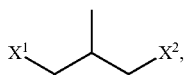

(3)

wherein $X^1$ and $X^2$ are the same as or different from each other
and each of $X^1$ and $X^2$ denotes a halogen atom,
to coupling reaction to obtain a 2,6-dimethyl-6-heptenyl halide compound of General Formula (4):

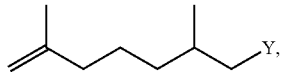

(4)

wherein Y is $X^1$ or $X^2$ as defined above;
converting the 2,6-dimethyl-6-heptenyl halide compound into a 2,6-dimethyl-6-heptenyl nucleophilic reagent of General Formula (5):

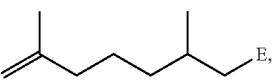

(5)

wherein E denotes Li or $MgZ^2$, wherein $Z^2$ denotes a halogen atom; and
subjecting the 2,6-dimethyl-6-heptenyl nucleophilic reagent to an addition reaction with at least one electrophilic reagent selected from the group consisting of formaldehyde, paraformaldehyde and 1,3,5-trioxane, followed by a hydrolysis reaction to obtain 3,7-dimethyl-7-octenol of Formula (6).

In another aspect of the invention, there is provided a method for producing a 3,7-dimethyl-7-octenyl carboxylate compound of General Formula (7):

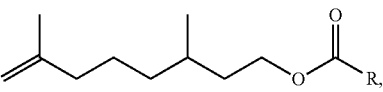

(7)

wherein R denotes a hydrogen atom or a monovalent hydrocarbon group having 1 to 6 carbon atoms.
comprising:
the steps in the above method to produce 3,7-dimethyl-7-octenol of Formula (6); and
a step of esterifying the 3,7-dimethyl-7-octenol to obtain the 3,7-dimethyl-7-octenyl carboxylate compound of General Formula (7).

According to the invention, 3,7-dimethyl-7-octenol and a 3,7-dimethyl-7-octenyl carboxylate compound can be simply, selectively and efficiently produced.

DETAILED DESCRIPTION OF THE PREFERRED EMBODIMENTS

The chemical formulae of intermediates, reagents and target compounds in the specification may include stereoisomers such as enantiomers and diastereomers in terms of structure. Unless otherwise stated, each chemical formula is intended to include all the isomers. The isomer may be used singly or as a mixture of two or more.

First, a step of subjecting a 3-methyl-3-butenyl nucleophilic reagent and a 1,3-dihalo-2-methylpropane compound to a coupling reaction to obtain a 2,6-dimethyl-6-heptenyl halide compound in a method for producing 3,7-dimethyl-7-octenol will be described. The 3-methyl-3-butenyl nucleophilic reagent is prepared, for example, from a 3-methyl-3-butenyl halide compound.

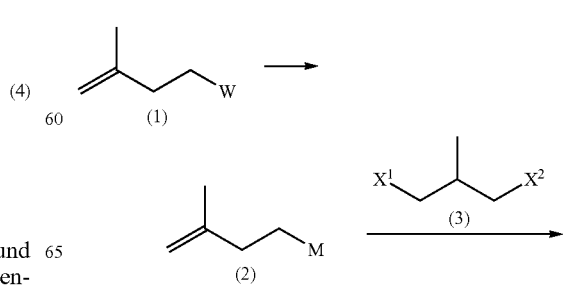

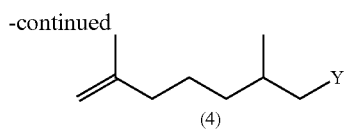

(4)

In the 3-methyl-3-butenyl halide compound of General Formula (1), W denotes a halogen atom, and examples of the halogen atom include a chlorine atom, a bromine atom, and an iodine atom. From the viewpoint of reactivity, a chlorine atom and a bromine atom are preferred.

Examples of the 3-methyl-3-butenyl halide compound (1) include 3-methyl-3-butenyl chloride, 3-methyl-3-butenyl bromide, and 3-methyl-3-butenyl iodide. From the viewpoint of easy preparation of the 3-methyl-3-butenyl nucleophilic reagent, compound stability and the like, 3-methyl-3-butenyl chloride and 3-methyl-3-butenyl bromide are preferred.

For the coupling reaction, an organometallic reagent containing a group I metal element, a group II metal element or a transition metal element is typically used.

In the 3-methyl-3-butenyl nucleophilic reagent of General Formula (2), M denotes Li, $MgZ^1$, $ZnZ^1$, Cu, $CuZ^1$, or $CuLiZ^1$, wherein $Z^1$ denotes a halogen atom or a 3-methyl-3-butenyl group.

The 3-methyl-3-butenyl nucleophilic reagent of General Formula (2) is preferably an organolithium reagent (3-methyl-3-butenyllithium) or an organomagnesium reagent (Grignard reagent, a 3-methyl-3-butenylmagnesium halide compound), particularly preferably the Grignard reagent, from the viewpoint of reactivity, selectivity, easy preparation, and the like.

Examples of the 3-methyl-3-butenylmagnesium halide compound include 3-methyl-3-butenylmagnesium chloride, 3-methyl-3-butenylmagnesium bromide, and 3-methyl-3-butenylmagnesium iodide.

The 3-methyl-3-butenyl nucleophilic reagent (2) may be typically prepared from a corresponding halide: a 3-methyl-3-butenyl halide compound (1), in a usual manner.

The 3-methyl-3-butenyl nucleophilic reagent containing a transition metal element to be used in the coupling reaction may be prepared by a metal exchange reaction in the presence of a stoichiometric amount (1 mol or more) of a transition metal compound which is contained by an organolithium reagent or an organomagnesium reagent, or may be formed in situ from an organolithium reagent or a Grignard reagent in the presence of a catalytic amount of a transition metal compound.

Examples of the transition metal compound include a transition metal compound containing copper, iron, nickel, palladium, zinc, silver, or the like. The transition metal compound is preferably a monovalent copper halide such as copper(I) chloride, copper(I) bromide and copper(I) iodide; a divalent copper halide such as copper(II) chloride, copper (II) bromide and copper(II) iodide; a copper cyanide such as copper(I) cyanide and copper(II) cyanide; a copper oxide such as copper(I) oxide and copper(II) oxide; or the other copper compounds such as dilithium tetrachlorocuprate ($Li_2CuCl_4$). The transition metal compound is particularly preferably a monovalent or divalent copper halide.

The amount of the transition metal compound is a catalytic amount (0.0001 to 0.999 mol) to a stoichiometric amount (1 mol) or an excess amount (more than 1 mol and not more than 100 mol), and a catalytic amount of the transition metal compound is particularly preferable.

When a transition metal compound is used in the coupling reaction, a cocatalyst including a phosphorus compound, for example, a trialkylphosphite such as triethylphosphite, and a triarylphosphine such as triphenylphosphine, may be used preferably in an amount of 0.001 to 1,000 parts relative to 100 parts of the transition metal compound from the viewpoint of improvement in solubility of the transition metal compound in a solvent.

In the step of coupling reaction, a lithium salt such as lithium chloride, lithium bromide and lithium iodide may be used as a reaction catalyst in an amount of 0.001 to 1,000 mol relative to 1 mol of the 1,3-dihalo-2-methylpropane compound (3) described later.

The amount of the 3-methyl-3-butenyl nucleophilic reagent (2) may be selected in consideration of, for example, the reagent type, conditions, reaction yield, economic efficiency such as the price of an intermediate, ease of isolation and purification of a target compound from a reaction product mixture. The amount of the 3-methyl-3-butenyl nucleophilic reagent (2) is preferably 0.2 to 100 mol, more preferably 0.5 to 20 mol, and even more preferably 0.8 to 2 mol relative to 1 mol of the 1,3-dihalo-2-methylpropane compound (3) described later.

In the 1,3-dihalo-2-methylpropane compound of General Formula (3), each of $X^1$ and $X^2$ denotes a halogen atom and preferably denotes a chlorine atom, a bromine atom, or an iodine atom.

From the viewpoint of reactivity, selectivity and the like, the combination of $X^1$ and $X^2$ is particularly preferably a combination of a bromine atom and a chlorine atom, a combination of a bromine atom and a bromine atom, a combination of an iodine atom and a chlorine atom, or a combination of an iodine atom and a bromine atom.

Examples of the 1,3-dihalo-2-methylpropane compound (3) preferably include 1,3-dichloro-2-methylpropane, 1-bromo-3-chloro-2-methylpropane, 1,3-dibromo-2-methylpropane, 1-iodo-3-chloro-2-methylpropane, 1-iodo-3-bromo-2-methylpropane, and 1,3-diiodo-2-methylpropane.

The coupling reaction may be carried out typically in a solvent under optional cooling or heating.

The solvent to be used for the coupling reaction is preferably an ether such as diethyl ether, di-n-butyl ether, t-butyl methyl ether, cyclopentyl methyl ether, tetrahydrofuran and 1,4-dioxane. As a mixed solvent, the ether may be mixed with a hydrocarbon such as hexane, heptane, benzene, toluene, xylene and cumene, or mixed with an aprotic polar solvent such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA).

The amount of the solvent is, but not limited to, preferably 10 to 1,000,000 ml, more preferably 100 to 100,000 ml, and even more preferably 150 to 10,000 ml relative to 1 mol of the 3-methyl-3-butenyl nucleophilic reagent (2).

The reaction temperature in the coupling reaction is preferably from −78° C. to the boiling point of a solvent and more preferably from −10 to 100° C.

The reaction time in the coupling reaction may be selected freely and is preferably optimized by tracking the reaction progress by gas chromatography (GC) or thin-layer chromatography (TLC). Typically, the reaction time is preferably 5 minutes to 240 hours.

In the 2,6-dimethyl-6-heptenyl halide compound of General Formula (4), Y is $X^1$ or $X^2$, and is explained above. When a combination of a bromine atom and a chlorine atom, a combination of a bromine atom and a bromine atom, a combination of an iodine atom and a chlorine atom, or a combination of an iodine atom and a bromine atom is used as the combination of $X^1$ and $X^2$, a chloride-atom-containing combination generally provides the chloride atom as Y and a chloride-atom-free combination generally provides the bromine atom as Y. Since the 2,6-dimethyl-6-heptenyl halide compound (4) is converted into the 2,6-dimethyl-6-heptenyl nucleophilic reagent (5) for the production of the 3,7-dimethyl-7-octenol (7), the 2,6-dimethyl-6-heptenyl halide compound (4) may be a mixture of compounds having different halogen atoms (i.e. different Ys).

Examples of the 2,6-dimethyl-6-heptenyl halide compound (4) include 2,6-dimethyl-6-heptenyl chloride, 2,6-dimethyl-6-heptenyl bromide, and 2,6-dimethyl-6-heptenyl iodide. From the viewpoint of reactivity, 2,6-dimethyl-6-heptenyl chloride and 2,6-dimethyl-6-heptenyl bromide are preferred.

When the 2,6-dimethyl-6-heptenyl halide compound (4) obtained in the coupling reaction has a sufficient purity, the crude product may be subjected to the subsequent step without purification, or may be purified by a method appropriately selected from purification methods commonly used in organic syntheses, such as distillation and various types of chromatography. The distillation is particularly preferred from the viewpoint of industrial cost efficiency.

Next, a step of converting the 2,6-dimethyl-6-heptenyl halide compound (4) into a 2,6-dimethyl-6-heptenyl nucleophilic reagent and a step of subjecting the 2,6-dimethyl-6-heptenyl nucleophilic reagent to an addition reaction with at least one electrophilic reagent selected from the group consisting of formaldehyde, paraformaldehyde and 1,3,5-trioxane, followed by an hydrolysis reaction to obtain 3,7-dimethyl-7-octenol in the method for producing 3,7-dimethyl-7-octenol will be described.

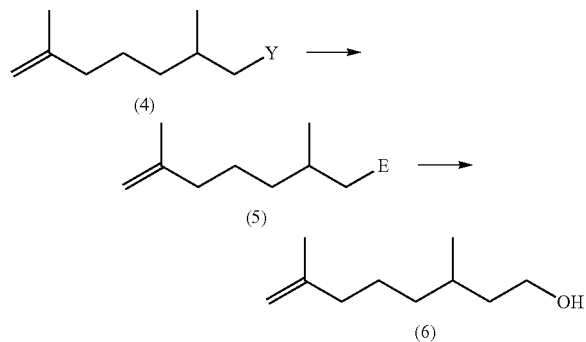

For the addition reaction, an organometallic reagent containing a group I metal element, a group II metal element or a transition metal element is typically used.

In the 2,6-dimethyl-6-heptenyl nucleophilic reagent of General Formula (5), E denotes Li or $MgZ^2$, wherein $Z^2$ denotes a halogen atom and is preferably Y.

The 2,6-dimethyl-6-heptenyl nucleophilic reagent (5) is, for example, preferably an organolithium reagent (2,6-dimethyl-6-heptenyllithium), or an organomagnesium reagent (Grignard reagent, a 2,6-dimethyl-6-heptenylmagnesium halide) from the viewpoint of reactivity, selectivity, ease of preparation and the like, and is particularly preferably a Grignard reagent.

Examples of the 2,6-dimethyl-6-heptenylmagnesium halide compound include 2,6-dimethyl-6-heptenylmagnesium chloride, 2,6-dimethyl-6-heptenylmagnesium bromide, and 2,6-dimethyl-6-heptenylmagnesium iodide.

The 2,6-dimethyl-6-heptenyl nucleophilic reagent (5) may be typically prepared from a corresponding halide: a 2,6-dimethyl-6-heptenyl halide compound, in a usual manner.

For the addition reaction, the transition metal compound as described above may be optionally used.

Examples of the electrophilic reagent to be used in the addition reaction include formaldehyde and a formaldehyde equivalent such as paraformaldehyde and 1,3,5-trioxane.

Formaldehyde may be used in the addition reaction, as a gas produced from the formaldehyde equivalent such as paraformaldehyde and 1,3,5-trioxane by heating or the like, or as a solution dissolved in a solvent to be used in the addition reaction described later. The formaldehyde equivalent such as paraformaldehyde and 1,3,5-trioxane may be directly used in the addition reaction. A mixture of formaldehyde with paraformaldehyde or 1,3,5-trioxane may also be used.

The amount of the electrophilic reagent may be selected in consideration of, for example, the reagent type, conditions, reaction yield, economic efficiency such as the price of an intermediate, ease of isolation and purification of a target compound from a reaction product mixture, and generation of by-products. The amount of the electrophilic reagent is preferably 0.8 to 100 mol, more preferably 0.9 to 10 mol, and even more preferably 1.0 to 2.0 mol relative to 1 mol of the 2,6-dimethyl-6-heptenyl nucleophilic reagent (5). Excess use of the electrophilic reagent may lead to generation of by-products including a formate ester (2,6-dimethyl-6-heptenyl formate) and a corresponding aldehyde (2,6-dimethyl-6-heptenal), and by-products (3,7-dimethyl-2-methylene-7-octenal, 2,2-dihydroxymethyl-3,7-dimethyl-7-octenol) generated further by the reaction of the aldehyde with an excess formaldehyde. As a result, the yield is lowered. Hence, excess use of the electrophilic reagent should be avoided.

The addition reaction is carried out typically in a solvent under optional cooling or heating.

The solvent to be used for the addition reaction is preferably an ether such as diethyl ether, di-n-butyl ether, t-butyl methyl ether, cyclopentyl methyl ether, tetrahydrofuran and 1,4-dioxane. The solvent may be used as a mixture of the ether with a hydrocarbon such as hexane, heptane, benzene, toluene, xylene and cumene, or with an aprotic polar solvent such as N,N-dimethylformnamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA).

The amount of the solvent is, but not limited to, preferably 10 to 1,000,000 ml, more preferably 100 to 100,000 ml, and even more preferably 150 to 10,000 ml relative to 1 mol of the 2,6-dimethyl-6-heptenyl nucleophilic reagent (5).

The reaction temperature in the addition reaction is preferably from −78° C. to the boiling point of a solvent and more preferably from −10 to 150° C. When the formaldehyde equivalent such as paraformaldehyde and 1,3,5-trioxane is used in the addition reaction, the reaction temperature is preferably 30 to 150° C. because the reaction proceeds while generating formaldehyde in the system.

The reaction time in the addition reaction may be selected freely and is preferably optimized by tracking the reaction progress by gas chromatography (GC) or thin-layer chromatography (TLC). Typically, the reaction time is preferably 5 minutes to 240 hours.

The 3,7-dimethyl-7-octenol of General Formula (6) is produced by hydrolysis reaction of a 3,7-dimethyl-7-octenoxide compound subsequently to the addition reaction.

The hydrolysis reaction typically proceeds through acidic work-up of a reaction product mixture obtained by the addition reaction.

Examples of the acid to be used in the hydrolysis reaction include ammonium chloride; an inorganic acid such as hydrochloric acid, hydrobromic acid, hydroiodic acid, sulfuric acid, nitric acid, boric acid and phosphoric acid; and an organic acid such as formic acid, acetic acid, propionic acid, oxalic acid, trifluoroacetic acid, methanesulfonic acid, benzenesulfonic acid, p-toluenesulfonic acid and naphthalenesulfonic acid. The acid is used singly or as a mixture of two or more.

The amount of the acid to be used in the hydrolysis reaction may be any amount sufficient for the reaction, and is preferably 1.0 to 100 mol relative to 1 mol of the 2,6-dimethyl-6-heptenyl nucleophilic reagent (5) from the viewpoint of satisfactory progress of the hydrolysis reaction.

When a formate ester (2,6-dimethyl-6-heptenyl formate) is present in such an amount as to interfere with an intended purpose together with 3,7-dimethyl-7-octenol (6), a crude product of 3,7-dimethyl-7-octenol (6) may be subjected to, for example, a hydrolysis reaction in a typical basic condition. As a result, the formate ester can be converted into 3,7-dimethyl-7-octenol (6).

Examples of the hydrolysis reaction in a typical basic condition include a hydrolysis reaction using an aqueous alkali metal hydroxide solution such as an aqueous sodium hydroxide solution.

The amount of the base to be used in the hydrolysis reaction may be any amount sufficient for the reaction, and is preferably 1.0 to 100 mol relative to 1 mol of the formate ester (2,6-dimethyl-6-heptenyl formate) from the viewpoint of satisfactory progress of the hydrolysis reaction.

When 3,7-dimethyl-7-octenol (6) obtained through the addition reaction and the hydrolysis reaction has a sufficient purity, the crude product may be used without purification to produce a 3,7-dimethyl-7-octenyl carboxylate compound, or may be purified by a method appropriately selected from purification methods commonly used in organic syntheses, such as distillation and various types of chromatography. The distillation is particularly preferred from the viewpoint of industrial cost efficiency.

Next, a step of esterifying the 3,7-dimethyl-7-octenol to obtain a 3,7-dimethyl-7-octenyl carboxylate compound in the method for producing a 3,7-dimethyl-7-octenyl carboxylate compound will be described.

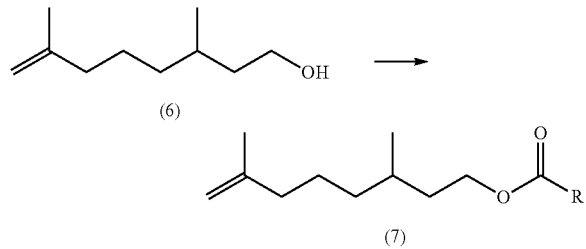

In the 3,7-dimethyl-7-octenyl carboxylate compound of General Formula (7), R denotes a hydrogen atom or a monovalent hydrocarbon group having 1 to 6 carbon atoms.

Examples of the monovalent hydrocarbon group having 1 to 6 carbon atoms include a linear alkyl group such as a methyl group, an ethyl group, an n-propyl group, an n-butyl group, an n-pentyl group and an n-hexyl group; a branched alkyl group such as an isopropyl group, an isobutyl group, an isopentyl group, an isohexyl group, a see-butyl group and a tert-butyl group; a cyclic alkyl group such as a cyclopentyl group, a cyclohexyl group, a 2-methylcyclopentyl group and a cyclopentylmethyl group; a linear, branched or cyclic alkenyl group such as a vinyl group, an allyl group, a 1-propenyl group, an isopropenyl group, a 1-methyl-1-propenyl group, a 2-methyl-1-propenyl group, an isopentenyl group and a cyclohexenyl group; and an aryl group such as a phenyl group.

The esterification may be carried out by a known esterification reaction or method such as a reaction with an acylating agent, a reaction with a carboxylic acid, transesterification, and a method in which 3,7-dimethyl-7-octenol (6) is converted into an alkylating agent and then the alkylating agent is reacted with a carboxylic acid.

Regarding the reaction with an acylating agent, 3,7-dimethyl-7-octenol (6) may be reacted with an acylating agent and a base sequentially or simultaneously in a single solvent or a mixture of two or more solvents.

Examples of the acylating agent preferably include an acyl halide such as acyl chloride and acyl bromide; a carboxylic acid anhydride; a mixed carboxylic acid anhydride such as a carboxylic trifluoroacetic anhydride, a carboxylic methanesulfonic anhydride, a carboxylic trifluoromethanesulfonic anhydride, a carboxylic benzenesulfonic anhydride and a carboxylic p-toluenesulfonic anhydride; and p-nitrophenyl carboxylate.

Examples of the acylating agent include propionyl chloride, crotonoyl chloride, benzoyl chloride and propionic anhydride.

The amount of the acylating agent is preferably 1 to 500 mol, more preferably 1 to 50 mol, and even more preferably 1 to 5 mol relative to 1 mol of 3,7-dimethyl-7-octenol (6).

Examples of the base to be used in the reaction with an acylating agent preferably include triethylamine, diisopropylethylamine, N,N-dimethylaniline, N,N-diethylaniline, pyridine, 2-ethylpyridine, and 4-dimethylaminopyridine.

The amount of the base is 1 to 500 mol relative to 1 mol of 3,7-dimethyl-7-octenol (6).

Examples of the solvent to be used in the reaction with an acylating agent include the above bases to be used as the solvents; chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; nitriles such as acetonitrile; ketones such as acetone and 2-butanone; esters such as ethyl acetate and n-butyl acetate; and aprotic polar solvents such as N,N-dimethylformamide, dimethylsulfoxide and hexamethylphosphoric triamide. The solvent may be used singly or as a mixture of two or more solvents selected from the above solvents.

The amount of the solvent is preferably 10 to 1,000,000 ml relative to 1 mol of 3,7-dimethyl-7-octenol (6).

The reaction using an acylating agent such as a carboxylic acid anhydride, a mixed carboxylic acid anhydride, and p-nitrophenyl carboxylate may also be carried out in the presence of an acid catalyst instead of the base.

Examples of the acid catalyst preferably include an inorganic acid such as hydrochloric acid, hydrobromic acid, sulfuric acid and nitric acid; an organic acid such as oxalic acid, trifluoroacetic acid, methanesulfonic acid, benzenesulfonic acid and p-toluenesulfonic acid; and a Lewis acid such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The amount of the acid catalyst to be used in the reaction with an acylating agent such as a carboxylic acid anhydride, a mixed carboxylic acid anhydride and p-nitrophenyl carboxylate is preferably 0.0001 to 100 mol relative to 1 mol of 3,7-dimethyl-7-octenol (6).

The reaction temperature in the reaction with an acylating agent may be selected appropriately depending on the type of an acylating agent and reaction conditions, and is typically preferably from −50° C. to the boiling point of a solvent and more preferably from −20° C. to room temperature (i.e. 5° C. to 35° C., the same applies hereinafter).

The reaction time in the reaction with an acylating agent is typically preferably from 5 minutes to 240 hours.

Regarding the reaction with a carboxylic acid, it is a dehydration reaction of 3,7-dimethyl-7-octenol (6) with the carboxylic acid, and is typically carried out in the presence of an acid catalyst.

When 3,7-dimethyl-7-octenol (6) is reacted with a carboxylic acid, the carboxylic acid is expressed as General Formula (8).

(8)

In the carboxylic acid of General Formula (8), R is already explained above.

Examples of the carboxylic acid include a linear saturated carboxylic acid such as formic acid, acetic acid, propionic acid, butyric acid, valeric acid and caproic acid; a branched saturated carboxylic acid such as isobutyric acid, isovaleric acid, 4-methylpentanoic acid, 2-methylbutanoic acid and pivalic acid; a linear unsaturated carboxylic acid such as acrylic acid, crotonic acid and 3-butenoic acid; a branched unsaturated carboxylic acid such as methacrylic acid, senecioic acid, tiglic acid, angelic acid, 3-methyl-4-pentenoic acid and 4-methyl-4-pentenoic acid; and an aromatic carboxylic acid such as benzoic acid.

The amount of the carboxylic acid is preferably 1 to 500 mol, more preferably 1 to 50 mol, and even more preferably 1 to 5 mol relative to 1 mol of 3,7-dimethyl-7-octenol (6).

When 3,7-dimethyl-7-octenol (6) is reacted with the carboxylic acid (8), an acid catalyst may be preferably used. Examples of the acid catalyst include an inorganic acid such as hydrochloric acid, hydrobromic acid, sulfuric acid and nitric acid; an organic acid such as oxalic acid, trifluoroacetic acid, methanesulfonic acid, benzenesulfonic acid and p-toluenesulfonic acid; and a Lewis acid such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The acid catalyst is used singly or as a mixture of two or more.

The amount of the acid catalyst is preferably 0.0001 to 100 mol, more preferably 0.001 to 1 mol, and even more preferably 0.01 to 0.05 mol relative to 1 mol of 3,7-dimethyl-7-octenol (6).

Examples and the amount of the solvent to be used in the reaction of 3,7-dimethyl-7-octenol (6) with the carboxylic acid (8) are the same as those in the reaction with the acylating agent.

The reaction temperature of 3,7-dimethyl-7-octenol (6) with the carboxylic acid (8) may be selected appropriately depending on reaction conditions, and is typically preferably from −50° C. to the boiling point of a solvent and more preferably from room temperature to the boiling point of a solvent. A solvent containing a hydrocarbon such as hexane, heptane, benzene, toluene, xylene and cumene may be used to allow the reaction to proceed while removing generated water from the system by azeotropy. In this case, the water may be distilled off with refluxing at the boiling point of the solvent at normal pressure. Alternatively, the water may be distilled off at a temperature lower than the boiling point under reduced pressure.

The reaction time in the reaction with the carboxylic acid is typically and preferably 5 minutes to 240 hours.

Regarding the transesterification, it is carried out by reacting 3,7-dimethyl-7-octenol (6) with an alkyl carboxylate in the presence of a catalyst, and removing the generated alcohol.

The alkyl carboxylate is preferably a primary alkyl ester of a carboxylic acid, and is particularly preferably a methyl carboxylate, an ethyl carboxylate, and an n-propyl carboxylate from the viewpoint of, for example, price and ease of progress of the reaction. Examples of the carboxylic acid include the same compounds as those of the carboxylic acid (8) in the esterification reaction with a carboxylic acid.

The amount of the alkyl carboxylate is preferably 1 to 500 mol, more preferably 1 to 50 mol, and even more preferably 1 to 5 mol relative to 1 mol of 3,7-dimethyl-7-octenol (6).

Examples of the catalyst to be used in the transesterification include an inorganic acid such as hydrochloric acid, hydrobromic acid, sulfuric acid and nitric acid; an organic acid such as oxalic acid, trifluoroacetic acid, methanesulfonic acid, benzenesulfonic acid and p-toluenesulfonic acid; a base such as sodium methoxide, sodium ethoxide, potassium t-butoxide and 4-dimethylaminopyridine; a salt such as sodium cyanide, potassium cyanide, sodium acetate, potassium acetate, calcium acetate, tin acetate, aluminum acetate, aluminum acetoacetate and alumina; and a Lewis acid such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The catalyst is used singly or as a mixture of two or more.

The amount of the catalyst is preferably 0.0001 to 100 mol, more preferably 0.001 to 1 mol, and even more preferably 0.01 to 0.05 mol relative to 1 mol of 3,7-dimethyl-7-octenol (6).

The transesterification may be carried out without a solvent (the alkyl carboxylate itself, which is a reaction reagent, may also be used as the solvent). The solvent-free reaction is preferable because it eliminates the necessity of additional operations such as concentration and solvent recovery. A solvent can be used supplementally.

Examples of the solvent to be used in the transesterification include hydrocarbons such as hexane, heptane, benzene, toluene, xylene and cumene; and ethers such as diethyl ether, dibutyl ether, diethylene glycol diethyl ether, diethylene glycol dimethyl ether, tetrahydrofuran and 1,4-dioxane. The solvent is used singly or as a mixture of two or more.

The amount of the solvent is preferably 10 to 1,000,000 ml relative to 1 mol of 3,7-dimethyl-7-octenol (6).

The reaction temperature in the transesterification may be selected appropriately depending on the type of alkyl carboxylate or reaction conditions. The transesterification is typically carried out with heating. The reaction is carried out at around the boiling point of a lower alcohol having 1 to 3 carbon atoms that is generated during the transesterification, while the generated lower alcohol is distilled off, so as to obtain good results. The lower alcohol has a low boiling point, and examples thereof include methanol, ethanol, and 1-propanol. The alcohol may be distilled off under reduced pressure at a temperature lower than the boiling point.

The reaction time in the transesterification is typically preferably 5 minutes to 240 hours.

Regarding the esterification method in which 3,7-dimethyl-7-octenol (6) is converted into an alkylating agent and then the alkylating agent is reacted with a carboxylic acid, 3,7-dimethyl-7-octenol (6) is converted into, for example, a corresponding halide (chloride, bromide, iodide) or a sulfonate (e.g. methanesulfonate, trifluoromethanesulfonate, benzenesulfonate, p-toluenesulfonate), and then reacted with a carboxylic acid typically in a solvent in the presence of a base.

Examples of the carboxylic acid include those of the carboxylic acid (8) to be used for the above esterification reaction with a carboxylic acid.

The amount of the carboxylic acid is preferably 1 to 500 mol, more preferably 1 to 50 mol, and even more preferably 1 to 5 mol relative to 1 mol of 3,7-dimethyl-7-octenol (6).

Examples and the amount of the solvent, examples and the amount of the base, the reaction time, and the reaction temperature with respect to the esterification method in which 3,7-dimethyl-7-octenol (6) is converted into an alkylating agent and then the alkylating agent is reacted with a carboxylic acid, are the same as those described in the esterification reaction of 3,7-dimethyl-7-octenol with an acylating agent.

In place of the carboxylic acid to be used in the reaction typically in a solvent in the presence of a base, a carboxylate salt such as sodium carboxylate, lithium carboxylate, potassium carboxylate and ammonium carboxylate may be used. The amount of the carboxylate salt is the same as the amount of the carboxylic acid to be used in the esterification reaction with a carboxylic acid.

The 3,7-dimethyl-7-octenyl carboxylate obtained in the esterification may be purified by a method appropriately selected from purification methods commonly used in organic syntheses, such as distillation and various types of chromatography. The distillation is preferred from the viewpoint of industrial cost efficiency.

As described above, a simple method for selectively and efficiently producing 3,7-dimethyl-7-octenol and a method for producing a 3,7-dimethyl-7-octenyl carboxylate compound are provided.

EXAMPLES

The invention will next be described in further detail with reference to Examples. It should not be construed that the invention is limited to or by them.

The purities of materials, products and intermediates are determined by gas chromatographic (GC) analysis and are expressed with "% GC". The GC conditions are as follows:
GC: Simadzu GC-14A;
Column: 5% Ph-Me silicone, 0.25 mmϕ×25 m;
Carrier gas: He;
Detector: FID.

Yields are expressed by conversion yields in accordance with the following equation in consideration of purities (% GC) of materials and products.

Conversion yield (%)=[(weight of product obtained by reaction×% GC)/molecular weight of the product]/[(weight of starting material in reaction×% GC)/molecular weight of the starting material]×100

The compound sample for spectrum measurements was prepared by purification of a crude product, as needed.

Example 1: Production No. 1 of 2,6-dimethyl-6-heptenyl chloride (Formula (4) Containing Cl as Y)

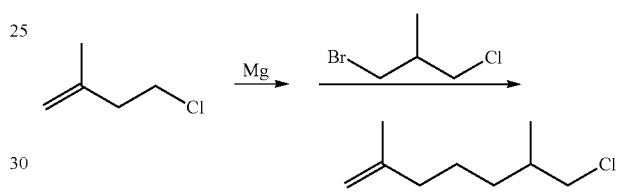

Under a nitrogen atmosphere, a solution of a Grignard reagent: 3-methyl-3-butenylmagnesium chloride in tetrahydrofuran was prepared from 441 g of 3-methyl-3-butenyl chloride (1) (99.6% GC), 600 ml of tetrahydrofuran and 102 g of magnesium. The Grignard reagent solution was added dropwise, while being stirred under a nitrogen atmosphere, to an ice-cooled mixture of 500 g of 1-bromo-3-chloro-2-methylpropane (99.9% GC), 5.85 g of copper(I) iodide, 11.8 g of triethylphosphite and 350 ml of tetrahydrofuran over 3 hours, while maintaining the temperature at 20° C. or less. The reaction mixture was stirred for 40 minutes, while being cooled by ice, and then a saturated aqueous ammonium chloride solution was added thereto to stop the reaction. The separated organic phase was subjected to common work-up including washing, drying and concentration to obtain a crude product. The crude product was distilled under reduced pressure to obtain 419 g of the target compound: 2,6-dimethyl-6-heptenyl chloride (Formula (4) containing Cl as Y) (up to 99.0% GC, conversion yield including initial distillate with low purity: 90%).

2,6-Dimethyl-6-heptenyl chloride (Formula (4) Containing Cl as Y)

Yellowish Oil
Boiling point: 64° C./800 Pa
IR (D-ATR): ν=3074, 2966, 2935, 2860, 1650, 1458, 887 cm$^{-1}$.
$^1$H-NMR (500 MHz, CDCl$_3$): δ=1.01 (3H, d, J=6.5 Hz), 1.15-1.27 (1H, m), 1.39-1.52 (3H, m), 1.71 (3H, s), 1.78-1.88 (1H, m), 2.01 (2H, br. t-like, J=~6 Hz), 3.41 (1H, dd, J=6.1, 10.7 Hz), 3.48 (1H, dd, J=5.3, 10.7 Hz), 4.67 (1H, br. s-like), 4.71 (1H, br. s-like) ppm.
$^{13}$C-NMR (125 MHz, CDCl$_3$): δ=17.75, 22.30, 24.75, 33.52, 35.43, 37.79, 51.14, 109.92, 145.68 ppm.

GC-MS (EI, 70 eV): 41, 56 (base peak), 69, 81, 95, 109, 124, 134, 145, 160 (M$^+$).

Example 2: Production No. 2 of 2,6-dimethyl-6-heptenyl chloride (Formula (4) containing Cl as Y)

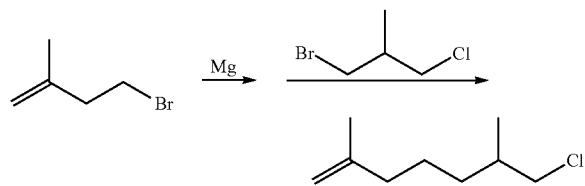

Under a nitrogen atmosphere, a mixture of 6.90 g of 3-methyl-3-butenyl bromide (1) (98.3% GC), 6.20 g of 1,2-dibromoethane (used for activation of magnesium) and 300 ml of tetrahydrofuran was added dropwise to a mixture of 5.70 g of magnesium and 10 ml of tetrahydrofuran to prepare a solution of a Grignard reagent: 3-methyl-3-butenylmagnesium bromide in tetrahydrofuran. The Grignard reagent was added dropwise, while being stirred under a nitrogen atmosphere, to an ice-cooled mixture of 35.5 g of 1-bromo-3-chloro-2-methylpropane, 240 mg of copper(I) iodide, 360 mg of triethylphosphite and 200 ml of tetrahydrofuran over 30 minutes, while maintaining the temperature at 25° C. or less. After the completion of the dropwise addition, the reaction mixture was warmed to room temperature and stirred at room temperature for 14 hours. Then the mixture was cooled by ice again, and a saturated aqueous ammonium chloride solution was added thereto to stop the reaction. The separated organic phase was subjected to common work-up including washing, drying and concentration to obtain 21.32 g of the target compound: 2,6-dimethyl-6-heptenyl chloride (Formula (4) containing Cl as Y) (up to 100% GC, conversion yield including initial distillate with low purity: 66%). The obtained product was the same as the product in Example 1.

Example 3: Production No. 1 of 3,7-dimethyl-7-octenol (6)

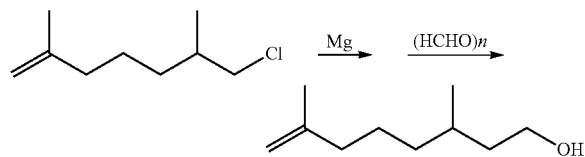

Under a nitrogen atmosphere, a solution of a Grignard reagent: 2,6-dimethyl-6-heptenylmagnesium chloride in tetrahydrofuran was prepared from 250 g of 2,6-dimethyl-6-heptenyl chloride (Formula (4) containing Cl as Y) (99.6% GC), 800 ml of tetrahydrofuran and 37.8 g of magnesium. A mixture (suspension) of 60 g of paraformaldehyde and 300 ml of tetrahydrofuran was added dropwise over 4 hours to the Grignard reagent solution which was being refluxed and stirred under a nitrogen atmosphere. After the completion of the dropwise addition, the reaction mixture was cooled to room temperature, then allowed to stand for 14 hours, and stirred and refluxed again for 30 minutes. The reaction mixture was cooled by ice, and a sufficient amount of a saturated aqueous ammonium chloride solution was added thereto to stop the reaction. The separated organic phase was subjected to common work-up by washing, drying and concentration to obtain 237 g of a crude product of the target compound: 3,7-dimethyl-7-octenol (6) (82.7% GC, yield: 81%). A part of the crude product was purified by silica gel column chromatography to obtain a sample (99.9% GC) for spectrum measurements.

3,7-Dimethyl-7-octenol (6)

Colorless Oil
Boiling point: 71° C./533 Pa
IR (D-ATR): ν=3329 (br.), 3073, 2931, 2872, 1650, 1456, 1365, 1057, 886 cm$^{-1}$.
$^1$H-NMR (500 MHz, CDCl$_3$): δ=0.88 (3H, d, J=6.7 Hz), 1.09-1.17 (1H, m), 1.25-1.34 (1H, m), 1.34-1.51 (3H, m), 1.64 (1H, s), 1.69 (3H, s), 1.98 (2H, br. t-like, J=~7 Hz), 3.61-3.71 (2H, m), 4.65 (1H, br. s-like), 4.68 (1H, br. s-like) ppm.
$^{13}$C-NMR (125 MHz, CDCl$_3$): δ=19.55, 22.30, 24.83, 29.34, 36.63, 37.95, 39.86, 61.07, 109.64, 146.07 ppm.
GC-MS (EI, 70 eV): 41, 55 (base peak), 67, 81, 95, 109, 123, 138, 156 (M$^+$).
GC-MS (CI, isobutane): 83, 97, 139, 157 [(M+1)$^+$, base peak].

Example 4: Production No. 2 of 3,7-dimethyl-7-octenol (6)

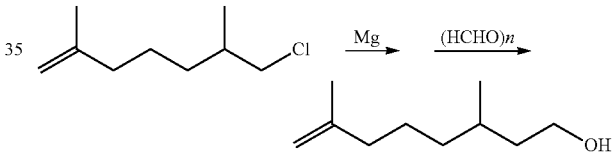

Under a nitrogen atmosphere, a solution of a Grignard reagent: 2,6-dimethyl-6-heptenylmagnesium chloride in tetrahydrofuran was prepared from 14.55 g of 2,6-dimethyl-6-heptenyl chloride (Formula (4) containing Cl as Y) (99.1% GC), 55 ml of tetrahydrofuran and 2.20 g of magnesium. A mixture (suspension) of 3.6 g of paraformaldehyde and 20 ml of tetrahydrofuran was added dropwise over 15 minutes to the Grignard reagent solution which was being stirred and refluxed under a nitrogen atmosphere. The reaction mixture was refluxed for 1 hour, then cooled to room temperature, and allowed to stand for 62 hours at room temperature. The reaction mixture was cooled by ice, subjected to addition of a sufficient amount of a saturated aqueous ammonium chloride solution to stop the reaction, and extracted with diethyl ether. The organic phase contained 3,7-dimethyl-7-octenol (6) as a target compound and 3,7-dimethyl-7-octenyl formate at a GC ratio of 77.6:22.4. The separated organic phase was subjected to addition of a sufficient amount of 25% by weight aqueous sodium hydroxide solution, and was refluxed with heating and stirring for 90 minutes to hydrolyze the contained 3,7-dimethyl-7-octenyl formate into the target compound: 3,7-dimethyl-7-octenol. Then the separated organic phase was subjected to common work-up including washing, drying and concentration, and then subjected to vacuum distillation to obtain 7.36 g of the target compound: 3,7-dimethyl-7-octenol (6) (up to 88.3% GC, conversion yield including initial distillate with low purity:

52%). The obtained target compound was the same as the target compound in Example 3.

3,7-Dimethyl-7-octenyl formate

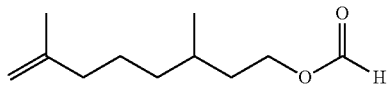

GC-MS (EI, 70 eV): 41, 55 (base peak), 67, 81, 95, 109, 123, 138, 184 (M$^+$).
GC-MS (CI, isobutane): 83 (base peak), 97, 139, 111, 125, 139, 185 [(M+1)$^+$].

Example 5: Production No. 1 of 3,7-dimethyl-7-octenyl propionate (Formula (7) Containing C$_2$H$_5$ as R)

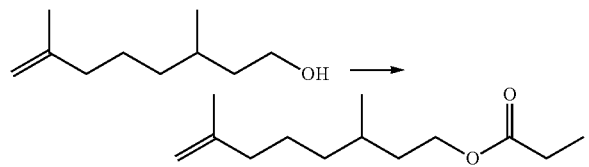

Under a nitrogen atmosphere, 153 g of propionyl chloride was added dropwise over 45 minutes to a mixture of 236 g of 3,7-dimethyl-7-octenol (6) (82.7% GC), 275 g of pyridine and 400 ml of toluene, the mixture being stirred. The resulting reaction mixture was allowed to stand at room temperature for 2 days, and then was stirred with cooling by ice. A saturated aqueous sodium hydrogen carbonate solution was added thereto to stop the reaction. The separated organic phase was subjected to common work-up including washing, drying and concentration to obtain 353 g of a crude product of 3,7-dimethyl-7-octenyl propionate (68.0% GC, yield: 90%). The crude product was distilled under reduced pressure to obtain 289 g of the target compound: 3,7-dimethyl-7-octenyl propionate (Formula (7) containing C$_2$H$_5$ as R) (up to 98.9% GC, conversion yield including initial distillate with low purity: 86%).

3,7-Dimethyl-7-octenyl propionate (Formula (7) Containing C$_2$H$_5$ as R)

Colorless Oil
Boiling point: 109° C./800 Pa
IR (D-ATR): ν=3329 (br.), 3073, 2933, 1740, 1650, 1463, 1351, 1187, 1083, 886 cm$^{-1}$.
$^1$H-NMR (500 MHz, CDCl$_3$): δ=0.90 (3H, d, J=6.7 Hz), 1.10-1.18 (1H, m), 1.23 (3H, t, J=7.5 Hz), 1.25-1.34 (1H, m), 1.35-1.50 (3H, m), 1.50-1.59 (1H, m), 1.61-1.69 (1H, m) 1.70 (3H-s), 1.97 (2H, br. t-like, J=~7 Hz), 2.30 (2H, q, J=7.5 Hz), 4.05-4.14 (2H, in), 4.65 (1H, br. s-like), 4.68 (1H, br. s-like) ppm.
$^{13}$C-NMR (125 MHz, CDCl$_3$): δ=9.12, 19.46, 22.30, 24.80, 27.61, 29.72, 35.48, 36.41, 37.92, 62.82, 109.72, 145.95, 174.54 ppm.
GC-MS (EI, 70 eV): 41, 57 (base peak), 69, 81, 95, 109, 123, 138, 157.
GC-MS (CI, isobutane): 83, 139 (base peak), 213 [(M+1)$^+$].

Example 6: Production No. 2 of 3,7-dimethyl-7-octenyl propionate (Formation (7) Containing C$_2$H$_5$ as R)

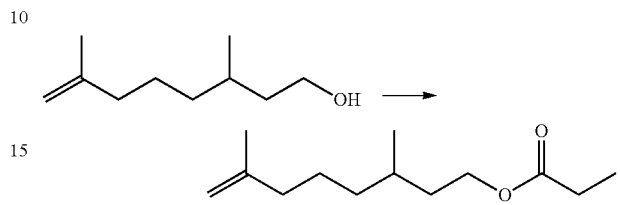

Under a nitrogen atmosphere, a mixture of 10.40 g of propionic anhydride and 20 ml of diethyl ether was added dropwise over 5 minutes to a mixture of 7.00 g of 3,7-dimethyl-7-octenol (6) (88.3% GC), 8.4 g of pyridine, 60 ml of diethyl ether and 10 mg of 4-dimethylaminopyridine, the latter mixture being cooled by ice and stirred. The resulting reaction mixture was stirred at room temperature for 14 hours, and then poured into a saturated aqueous sodium hydrogen carbonate solution to stop the reaction. The separated organic phase was subjected to common work-up including washing, drying and concentration, and then subjected to vacuum distillation to obtain 7.69 g of the target compound: 3,7-dimethyl-7-octenyl propionate (Formula (7) in which R is C$_2$H$_5$) (86.4 to 98.9% GC, conversion yield: 81%). The obtained target compound was the same as the target compound in Example 5.

Example 7: Production of 3,7-dimethyl-7-octenyl benzoate (Formula (7) Containing phenyl as R)

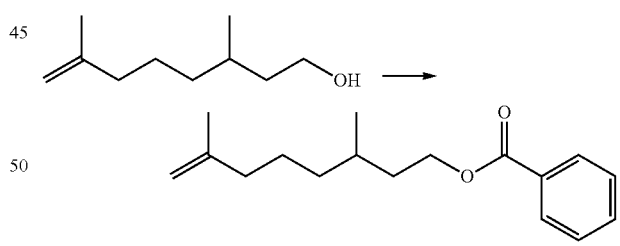

Under a nitrogen atmosphere, a mixture of 2.20 g of benzoyl chloride and 10 ml of diethyl ether was added dropwise over 5 minutes to a mixture of 2.00 g of 3,7-dimethyl-7-octenol (92.1% GC) and 10 g of pyridine, the latter mixture being stirred. The resulting reaction mixture was stirred at room temperature for 30 minutes, and then poured into water to stop the reaction. The separated organic phase was subjected to common work-up including washing, drying and concentration, and then subjected to vacuum distillation to obtain 2.87 g of the target compound: 3,7-dimethyl-7-octenyl benzoate (Formula (7) containing phenyl as R) (95.8 to 98.3% GC, conversion yield: 90%).

3,7-Dimethyl-7-octenyl benzoate (Formula (7) Containing phenyl as R)

Colorless Oil
Boiling point: 118° C./399 Pa
IR (D-ATR): ν=3072, 2959, 2932, 1792, 1721, 1452, 1274, 1111, 886 cm$^{-1}$.
$^1$H-NMR (500 MHz, CDCl$_3$): δ=0.92 (3H, d, J=6.5 Hz), 1.16-1.24 (1H, m), 1.34-1.54 (3H, m), 1.55-1.63 (1H, m), 1.63-1.70 (1H, m), 1.71 (3H, s), 1.78-1.85 (1H, m), 2.00 (2H, br. t-like, J=~7 Hz), 4.32-4.41 (2H, m), 4.67 (1H, br. s-like), 4.70 (1H, br. s-like), 7.44 (2H, t-like, J=8 Hz), 7.55 (1H, t-like, J=7.5 Hz), 8.04 (2H, d-like, J=7 Hz) ppm.
$^{13}$C-NMR (125 MHz, CDCl$_3$): δ=19.54, 22.32, 24.82, 29.86, 35.54, 36.45, 37.92, 63.47, 109.75, 128.28, 129.48, 130.47, 132.76, 145.95, 166.64 ppm.
GC-MS (EI, 70 eV): 41, 55, 77, 105 (base peak), 123, 138, 205.

Example 8: Production of 3,7-dimethyl-7-octenyl crotonate (Formula (7) Containing CH(CH)CH$_3$ as R)

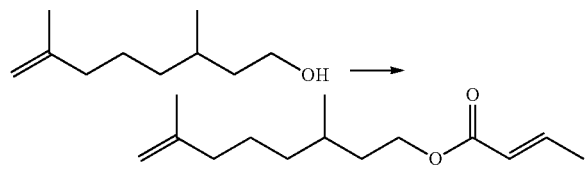

Under a nitrogen atmosphere, a mixture of 2.50 g of crotonoyl chloride and 20 ml of toluene was added dropwise over 5 minutes to a mixture of 2.50 g of 3,7-dimethyl-7-octenol (6) (92.1% GC) and 12 g of pyridine, the latter mixer being stirred. The resulting reaction mixture was stirred with cooling by ice for 3 hours, and then poured into water to stop the reaction. The separated organic phase was subjected to common work-up including washing, drying and concentration, and then subjected to vacuum distillation to obtain 2.50 g of a target compound: 3,7-dimethyl-7-octenyl crotonate (Formula (7) containing CH(CH)CH$_3$ as R) (94.5% GC, the ratio of E-isomer to Z-isomer is 94:6, conversion yield: 76%).

3,7-Dimethyl-7-octenyl crotonate (Formula (7) Containing CH(CH)CH$_3$ as R) (the Ratio of E-Isomer to Z-Isomer is 94:6)

Yellowish Oil
Boiling point: 83° C./399 Pa
IR (D-ATR): ν=3074, 2933, 2872, 1723, 1660, 1650, 1445, 1312, 1294, 1265, 1182, 1103, 969, 886 cm$^{-1}$.
$^1$H-NMR (500 MHz, CDCl$_3$), spectrum of major E-isomer: δ=0.91 (3H, d, J=6.8 Hz), 1.11-1.18 (1H, m), 1.27-1.35 (1H, m), 1.36-1.51 (3H, m), 1.51-1.61 (1H, m), 1.64-1.72 (1H, m), 1.70 (3H, s), 1.86 (3H, dd, J=1.7, 7.1 Hz), 1.98 (2H, br. t-like, J=~8 Hz), 4.11-4.19 (2H, m), 4.65 (1H, br. s-like), 4.68 (1H, br. s-like), 5.83 (1H, dq, J=15.5, 1.7 Hz), 6.95 (1H, dq, J=15.5, 6.9 Hz) ppm.
$^{13}$C-NMR (125 MHz, CDCl$_3$), spectrum of major E-isomer: δ=17.90, 19.46, 22.31, 24.80, 29.73, 35.51, 36.43, 37.93, 62.65, 109.71, 122.79, 144.33, 145.98, 166.61 ppm.
GC-MS (EI, 70 eV): 41, 55, 69 (base peak), 81, 95, 109, 123, 138, 224 (M$^+$). Both the E-isomer and the Z-isomer exhibited substantially the same mass spectrum where slight differences were observed in terms of fragment intensity.

The invention claimed is:
1. A method for producing 3,7-dimethyl-7-octenol of Formula (6):

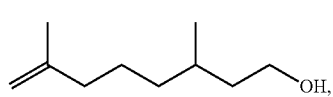

comprising:
subjecting a 3-methyl-3-butenyl nucleophilic reagent of General Formula (2):

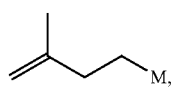

wherein M denotes Li, MgZ$^1$, ZnZ$^1$, Cu, CuZ$^1$, or CuLiZ$^1$, wherein
Z$^1$ denotes a halogen atom or a 3-methyl-3-butenyl group, and a 1,3-dihalo-2-methylpropane compound of General Formula (3):

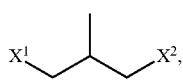

wherein X$^1$ and X$^2$ are the same as or different from each other,
and each of X$^1$ and X$^2$ denotes a halogen atom, to a coupling reaction to obtain a 2,6-dimethyl-6-heptenyl halide compound of General Formula (4):

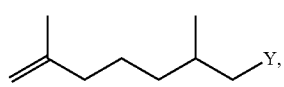

wherein Y is X$^1$ or X$^2$ as defined above;
converting the 2,6-dimethyl-6-heptenyl halide compound into a 2,6-dimethyl-6-heptenyl nucleophilic reagent of General Formula (5):

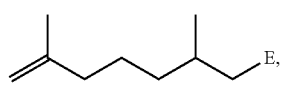

wherein E denotes Li or MgZ$^2$, wherein Z$^2$ is a halogen atom; and
subjecting the 2,6-dimethyl-6-heptenyl nucleophilic reagent to an addition reaction with at least one electrophilic reagent selected from the group consisting of formaldehyde, paraformaldehyde and 1,3,5-trioxane, followed by a hydrolysis reaction to obtain the 3,7-dimethyl-7-octenol of Formula (6).

2. The method for producing 3,7-dimethyl-7-octenol according to claim 1, further comprising a step of converting a 3-methyl-3-butenyl halide compound of General Formula (1):

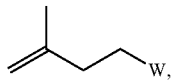
(1)

wherein W denotes a halogen atom, into the 3-methyl-3-butenyl nucleophilic reagent of General Formula (2).

3. A method for producing a 3,7-dimethyl-7-octenyl carboxylate compound of General Formula (7):

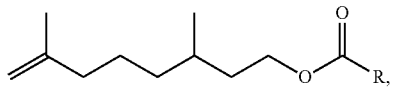
(7)

wherein R denotes a hydrogen atom or a monovalent hydrocarbon group having 1 to 6 carbon atoms, comprising:
the steps of claim 1 to produce 3,7-dimethyl-7-octenol; and
a step of esterifying the 3,7-dimethyl-7-octenol to obtain the 3,7-dimethyl-7-octenyl carboxylate compound of General Formula (7).

4. A method for producing a 3,7-dimethyl-7-octenyl carboxylate compound of General Formula (7):

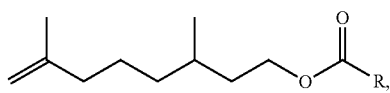
(7)

wherein R denotes a hydrogen atom or a monovalent hydrocarbon group having 1 to 6 carbon atoms, comprising:
the steps of claim 2 to produce 3,7-dimethyl-7-octenol; and
a step of esterifying the 3,7-dimethyl-7-octenol to obtain the 3,7-dimethyl-7-octenyl carboxylate compound of General Formula (7).

* * * * *